United States Patent [19]
Ojima et al.

[11] Patent Number: 5,017,718
[45] Date of Patent: May 21, 1991

[54] PROCESS FOR PREPARING POLYFLUOROALKYL-SUBSTITUTED COMPOUNDS

[75] Inventors: Iwao Ojima, New York, N.Y.; Takamasa Fuchikami, Kanagawa, Japan

[73] Assignee: Sagami Chemical Research Center, Tokyo, Japan

[21] Appl. No.: 574,214

[22] Filed: Jan. 26, 1984

[30] Foreign Application Priority Data

Jan. 26, 1983 [JP] Japan ................................ 58-9940
Feb. 16, 1983 [JP] Japan ................................ 58-22813

[51] Int. Cl.$^5$ .......................... C07F 7/08; C07F 7/10; C07F 7/18; C07F 21/18
[52] U.S. Cl. ................................ 556/466; 556/413; 556/415; 556/419; 556/427; 556/436; 556/440; 556/470; 556/476; 570/135; 570/136; 570/137; 570/153; 570/154; 570/172; 570/175; 204/157.63; 204/157.64; 204/157.65; 564/192; 564/193; 564/199; 564/204; 564/209; 564/463; 564/502; 564/509; 564/510; 568/39; 568/41; 568/42; 568/43; 568/44; 568/56; 568/307; 568/382; 568/416; 568/495; 568/417; 568/418; 568/419; 568/589; 568/683; 568/684; 568/685; 558/357; 558/359; 560/156; 560/160; 560/161; 560/174; 560/183; 560/205; 560/226; 560/227

[58] Field of Search ............... 556/466, 470, 413, 415, 556/419, 426, 427, 440, 436; 570/135, 136, 137, 153, 154, 172, 175; 204/157.63, 157.64, 157.65; 558/357, 359; 564/510, 192, 193, 199, 204, 209, 463, 502, 509; 568/39, 41, 42, 43, 44, 56, 307, 382, 416, 495, 417, 418, 419, 589, 683, 684, 685; 560/156, 160, 161, 174, 183, 205, 226, 227

[56] References Cited

FOREIGN PATENT DOCUMENTS 0005368 4/1972 Japan .
0037644 5/1975 Japan .
0008683 3/1978 Japan .

Primary Examiner—Paul F. Shaver
Attorney, Agent, or Firm—Sughrue, Mion, Zinn, Macpeak & Seas

[57] ABSTRACT

A process for preparing a perfluoroalkyl-substituted compound is disclosed. The process comprises reacting a halopolyfluoroalkane having 1 to 20 carbon atoms with a compound selected from the group consisting of (1) a substituted or unsubstituted ethylene, (2) a substituted or unsubstituted acetylene and (3) a substituted or unsubstituted allylsilane, in the presence of a metal-carbonyl complex of the metal of the Group VIII of the Periodic Table. Alternatively, the reaction between the halopolyfluoroalkane and the substituted or unsubstituted allylsilane is effected under radical generating condition.

15 Claims, No Drawings

PROCESS FOR PREPARING POLYFLUOROALKYL-SUBSTITUTED COMPOUNDS

FIELD OF THE INVENTION

This invention relates to a process for preparing polyfluoroalkyl-substituted compounds. More specifically, it relates to a process for preparing polyfluoroalkyl-substituted compounds which comprises reacting a halopolyfluoroalkane having 1 to 20 carbon atoms with a compound selected from the group consisting of (1) a substituted or unsubstituted ethylene, (2) a substituted or unsubstituted acetylene and (3) a substituted or unsubstituted allylsilane, in the presence of a metal-carbonyl complex of the metal of the Group VIII of the Periodic Table.

BACKGROUND OF THE INVENTION

The polyfluoroalkyl-substituted compounds obtained by the process of this invention can be represented by the following formulae:

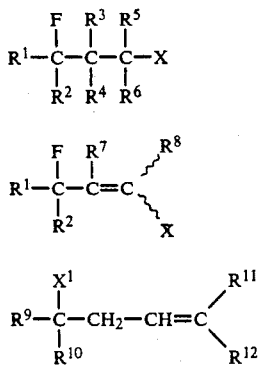

wherein:

X represents a chlorine atom, a bromine atom or an iodine atom;

$R^1$ and $R^2$ each represents hydrogen, a halogen atom (F, Cl, Br or I) or a poly- or perfluoroalkyl group having 1 to 20 carbon atoms;

$R^3$, $R^4$, $R^5$, $R^6$, $R^7$ and $R^8$ each represents hydrogen; a halogen atom (F, Cl, Br or I); a poly- or perfluorocarbon group having 1 to 20 carbon atoms; or a substituted or unsubstituted alkyl, vinyl, aryl, alkyloxy, acyloxy, amino, amide, silyl, silyloxy, alkylthio, alkoxycarbonyl, acyl, formyl or cyano group wherein the alkyl group has 1 to 10 carbon atoms and wherein the substituent is selected from the group consisting of an alkyl group having 1 to 5 carbon atoms, a halogen atom, an alkoxy group having 1 to 5 carbon atoms, a trialkylsilyl or trialkylsilyloxy group having 1 to 5 carbon atoms in each alkyl moiety, a hydroxy group, an alkoxycarbonyl group having 1 to 5 carbon atoms in the alkoxy moiety and an aryl group;

$R^9$ and $R^{10}$ each represents hydrogen, a halogen atom (F, Cl, Br or I) or a poly- or perfluoroalkyl group having 1 to 20 carbon atoms;

$R^{11}$ and $R^{12}$ each represents hydrogen, an alkyl group having 1 to 10 carbon atoms or an aryl group;

$X^1$ represents a halogen atom (F, Cl, Br or I); and wherein at least one of $R^9$, $R^{10}$ and $X^1$ represents a fluorine atom or a poly- or perfluoroalkyl group having 1 to 20 carbon atoms.

The polyfluoroalkyl-substituted compounds of the formulae (III) and (V) are useful as intermediates for surface active agents, water-repellents, oil-repellents, fiber treating agents, etc. as disclosed in, for example, Japanese Patent Publication (Examined) Nos. 37644/75 and 8683/78, U.S. Pat. No. 3,979,469 and British Patent No. 1,411,200, and the polyfluoroalkyl-substituted compounds of the formula (VIII), i.e., 3-polyfluoroalkyl-1-propenes, are useful as intermediates for fiber treating agents as disclosed in U.S. Pat. No. 3,843,735 and British Patent No. 1,377,235.

Hitherto, polyfluoroalkyl-substituted compounds of the formulae (III) and (V) have been prepared by (1) a method comprising radiating a mixture of an iodoperfluoroalkane and an olefin or an acetylene compound with light as disclosed in, for example, R. N. Haszeldine, J. Chem. Soc., 2856 (1949); and ibid, 3037 (1950), (2) a method comprising reacting an iodoperfluoroalkane with an olefin or an acetylene compound at a temperature higher than 200° C. as disclosed in, for example, R. N. Haszeldine, J. Chem. Soc., 2789 (1950); and R. N. Haszeldine and B. R. Steele, J. Chem. Soc., 1199 (1953), (3) a method comprising heat-reacting an iodoperfluoroalkane with an olefin or an acetylene compound in the presence of a radical reaction initiator as disclosed in, for example, K. Baum, C. D. Bedford and R. J. Hunadi, J. Org. Chem., 47, 2251, or (4) a method comprising reacting a haloperfluoroalkane with an olefin in the presence of an amine and a metal salt of the Group Ia to IVa, Ib to VIIb or VIII of the Periodic Table or in the presence of an amine-metal salt complex as disclosed in Japanese Patent Publication (Unexamined) No. 5368/72, Japanese Patent Publication (Examined) Nos. 37644/75 and 8683/78.

However, the above conventional method (1) requires radiation with light for a prolonged period of time and has a disadvantage in that the yield of the desired product is not satisfactory. Also, the above conventional method (2) requires a reaction at a high temperature for a long period of time in order to obtain the desired product in a satisfactory yield and, further, it requires a reactor which is resistant to high temperature and high pressure. The above conventional method (3) requires a reaction at a high reaction temperature for a long period of time and also requires a radical reaction initiator which is unstable and dangerous and, therefore, which must be handled with great care. In addition, the radical reaction initiator used in the method (3) is not recovered for reuse. The above conventional method (4) requires a reaction at a high temperature for a long period of time and, further, the yield of the desired product is generally poor, as evidenced by Comparative Examples hereinafter described.

On the other hand, the 3-polyfluoroalkyl-1-propenes of the formula (VIII) have been conventionally prepared by a method comprising adding a perfluoroalkyl iodide to an allyl alkyl ether or an allyl ester to prepare the corresponding 3-perfluoroalkyl-2-iodo-1-propyl alkyl ether or 3-perfluoroalkyl-2-iodo-1-propyl ester, respectively, followed by treating the resulting ether or ester with zinc as disclosed in Japanese Patent Publication (Unexamined) No. 34805/73. However, this conventional method requires the reactions in two steps and also gives the product in poor yield. Further, the starting material used in this conventional method is limited to compounds having a perfluoroalkyl group, and, therefore, starting compounds having a halopolyfluoroalkyl group cannot be used in this method.

DETAILED DESCRIPTION OF THE INVENTION

As a result of extensive studies on a process for preparing polyfluoroalkyl-substituted compounds from commercially available starting materials without causing disadvantages of the conventional methods as described above, the present inventors have found that the polyfluoroalkyl-substituted compounds of the formulae (III), (V) and (VIII) can be prepared in a satisfactory yield by reaction under mild reaction conditions for a short period of time, using a metal-carbonyl complex of the metal of the Group VIII of the Periodic Table as a catalyst.

Further, the present inventors have found that the polyfluoroalkyl-substituted compounds of the formula (VIII) can also be prepared in a simple reaction step in good yield by reaction under radical generating conditions, as described hereinafter in detail.

The process according to the present invention can be represented by the following reaction scheme:

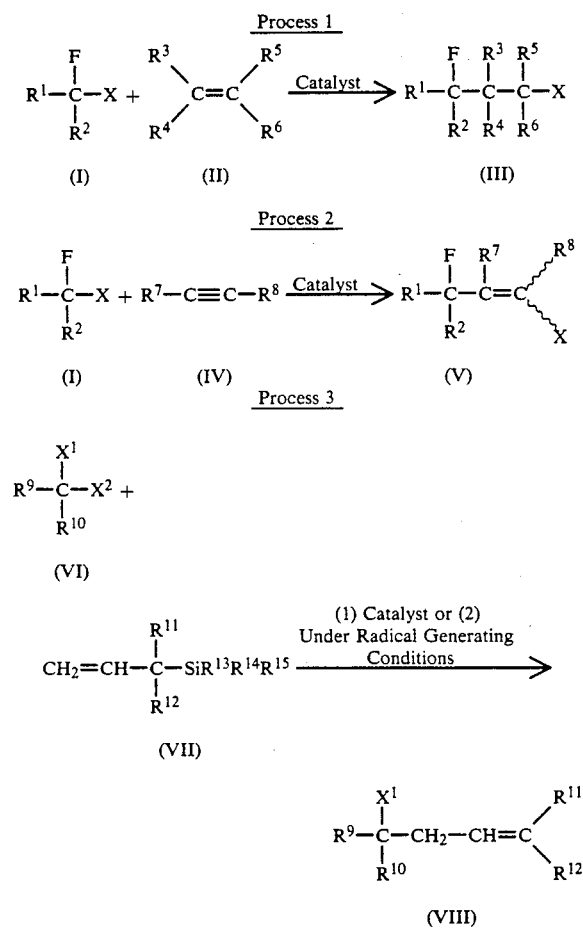

wherein:

X and $X^2$ each represents a chlorine atom, a bromine atom or an iodine atom;

$R^1$ and $R^2$ each represents hydrogen, a halogen atom or a poly- or perfluoroalkyl group having 1 to 20 carbon atoms;

$R^3$, $R^4$, $R^5$, $R^6$, $R^7$ and $R^8$ each represents hydrogen; a halogen atom; a poly- or perfluorocarbon group having 1 to 20 carbon atoms; or a substituted or unsubstituted alkyl, vinyl, aryl, alkyloxy, acyloxy, amino, amide, silyl, silyloxy, alkylthio, alkoxycarbonyl, acyl, formyl or cyano group wherein the alkyl group has 1 to 10 carbon atoms and wherein the substituent is selected from the group consisting of an alkyl group having 1 to 5 carbon atoms, a halogen atom, an alkoxy group having 1 to 5 carbon atoms, a trialkylsilyl or trialkylsilyloxy group having 1 to 5 carbon atoms in each alkyl moiety, a hydroxy group, an alkoxycarbonyl group having 1 to 5 carbon atoms in the alkoxy moiety and an aryl group;

$R^9$ and $R^{10}$ each represents hydrogen, a halogen atom or a poly- or perfluoroalkyl group having 1 to 20 carbon atoms;

$R^{11}$, $R^{12}$, $R^{13}$, $R^{14}$ and $R^{15}$ each represents hydrogen, an alkyl group having 1 to 10 carbon atoms or an aryl group;

$X^1$ represents a halogen atom; and wherein at least one of $R^9$, $R^{10}$ and $X^1$ represents a fluorine atom or a poly- or perfluoroalkyl group having 1 to 20 carbon atoms.

The term "aryl" as used herein includes, for example, a phenyl group, a tolyl group, an anisyl group, a p-chlorophenyl group, a pentafluorophenyl group, a naphthyl group and the like.

The starting materials (I) used in the processes 1 and 2 of the present invention are halopolyfluoroalkanes having 1 to 20 carbon atoms and include iodotrifluoromethane, 1-iodopentafluoroethane, 1-iodoheptafluoropropane, 1-iodononafluorobutane, 1-iodoperfluoroheptane, 1-iodoperfluorooctane, 1-iodoperfluorodecane, 2-iodoheptafluoropropane, 2-bromo-1-iodotetrafluoroethane, 1,2-dichloro-1-iodotrifluoroethane, 1,2-diiodotetrafluoroethane, 1-chloro-2-iodo-1,1,2-trifluoroethane, 1,4-diiodoperfluorobutane, 1,6-diiodoperfluorohexane, 1,8-diiodoperfluorooctane, 2-nonafluorobutyl-1,1-difluoro-1-iodoethane, 1,3,3,3-tetrafluoro-1-iodopropane, difluorodibromomethane, trifluorobromomethane, bromochlorodifluoromethane, 1,2-dibromotetrafluoroethane, 1-chloro-1,2-dibromotrifluoroethane, 1,2-dibromohexafluoropropane, 1-bromopentafluoroethane, 1-bromoheptafluoropropane, 1-bromoperfluorohexane and the like. These compounds are commercially available.

The starting materials (VI) used in the Process 3 of the present invention are halopolyfluoroalkanes having 1 to 20 carbon atoms and include those used in the Processes 1 and 2 described above and, additionally, 1,1,1-trifluorotrichloroethane, 1,1,1-trifluorotribromoethane, 1,1-difluorotetrachloroethane, 2,2-dibromohexafluoropropane, 1,1,3,3-tetrafluorotetrachloropropane and the like. These compounds are also commercially available.

The unsubstituted or substituted ethylene of the formula (II) used in the Process 1 include, for example, ethylene, propylene, 1-butene, 1-pentene, 1-hexene, vinyl chloride, vinyl bromide, vinyl acetate, vinyl ethyl ether, vinyloxytrimethylsilane, vinyl ethyl sulfide, N-vinyl-2-pyrrolidinone, vinyltrimethylsilane, styrene, vinylpyridine, butadiene, isoprene, piperylene, allyl alcohol, allylamine, allylmercaptan, allyl acetate, allyloxytrimethylsilane, methyl vinylacetate, ethyl acrylate, acrolein, acrylonitrile, 1-penten-3-ol, 3-buten-1-ol, acrolein diethyl acetal, 2-allyloxyethanol, allylbenzene, trifluoropropene, heptafluoropropylethylene, 2-butene, cylohexene, 3-hexene, methyl crotonate, 2-buten-1,4-diol, isobutylene, 2-methyl-2-butene, vinyl fluoride, vinylidene fluoride, trifluoroethylene, tetrafluoroethylene, hexafluoropropene and the like. These compounds are commercially available.

The unsubstituted or substituted acetylene compounds of the formula (IV) used in the Process 2 include, for example, acetylene, propyne, butyne, heptyne, phenylacetylene, trimethylsilylacetylene, propargyl alcohol, 3-butyn-1-ol, methyl propiolate, trifluoropropyne, bis(trimethylsilyl)acetylene, 2-butyne, hexafluoro-2-butyne, 3-hexyne, 2-butyn-1,4-diol, dimethyl acetylenedicarboxylate and the like. These compounds are also commercially available.

The allylsilane compounds of the formula (VII) used in the Process 3 include, for example, allyltrimethylsilane, allyltriphenylsilane, allyldimethylphenylsilane, allylmethyldiphenylsilane, (1-methyl-2-propenyl)trimethylsilane, (1-ethyl-2-propenyl)trimethylsilane, (1-phenyl-2-propenyl)trimethylsilane, (1,1-dimethyl-2-propenyl)dimethylsilane, (1,1-dimethyl-2-propenyl)trimethylsilane, (1,1-dimethyl-2-propenyl)diphenylsilane, (1,1-dimethyl-2-propenyl)triphenylsilane, (1-trifluoromethyl-2-propenyl)trimethylsilane, 3-trimethylsilyl-5,5,5-trifluoro-1-pentene and the like. These compounds are commercially available.

The reactions according to the Processes 1 to 3 above are carried out in the presence of a carbonyl complex of a metal of the Group VIII of the Periodic Table. Examples of such metal-carbonyl complexes are iron-carbonyl complexes such as $Fe(CO)_5$, $Fe_2(CO)_9$, $Fe_3(CO)_{12}$, $C_4H_6Fe(CO)_3$, $C_4H_4Fe(CO)_3$, $[C_5H_5Fe(CO)_2]_2$, $[Et_3NH][HFe_3(CO)_{11}]$, $PyFe(CO)_4$ and the like, ruthenium-carbonyl complexes such as $Ru_3(CO)_{12}$, $[RuCl_2(CO)_3]_2$ and the like, cobalt-carbonyl complexes such as $Co_2(CO)_3$, $Co_4(CO)_{12}$, $C_5H_5Co(CO)_2$, $[Ph_3PCo(CO)_3]_2$ and the like, rhodium-carbonyl complexes such as $Rh_6(CO)_{16}$, $Rh_4(CO)_{12}$, $HRh(CO)(PPh_3)_3$, $[PhCl(CO)_2]_2$, $RhCl(CO)(PPh_3)_2$ and the like, nickel-carbonyl complexes such as $Ni(CO)_4$, $Ni(PPh_3)_2(CO)_2$ and the like, iridiumcarbonyl complexes such as $Ir(CO)_{12}$, $IrI(CO)(PPh_3)_2$, $HIr(CO)(PPh_3)_3$ and the like, wherein Py represents pyridine, Et represents ethyl and Ph represents phenyl. Of these complexes, iron-, cobalt- or ruthenium-carbonyl complexes are preferred from the standpoint of yield of the desired product. The metal-carbonyl complex can be used in an amount ranging from about 1/10,000 to about 1 mol per mol of the halopolyfluoroalkane (I) or (VI), but is preferably used in an amount of from 1/1,000 to 1/10 mol per mol of (I) or (IV) in order to perform the reaction smoothly and economically.

The reactions according to Processes 1 to 3 can be carried out effectively in the presence of an amine. Examples of amines which can be used include primary amines such as methylamine, ethylamine, propylamine, isopropylamine, butylamine, amylamine, hexylamine, heptylamine, octylamine, nonylamine, decylamine, undecylamine, dodecylamine, tridecylamine, tetradecylamine, pentadecylamine, cetylamine, allylamine, cyclopropylamine, cyclobutylamine, cyclopentylamine, cyclohexylamine, aniline, benzylamine, toluidine, naphthylamine and the like, secondary amines such as dimethylamine, diethylamine, dipropylamine, diisopropylamine, dibutylamine, diamylamine, diallylamine, methylaniline, ethylaniline, dibenzylamine, diphenylamine, piperazine, piperidinone and the like, tertiary amines such as trimethylamine, triethylamine, tripropylamine, tributylamine, triamylamine, dimethylethylamine, triallylamine, dimethylaniline, diethylaniline, tribenzylamine and the like, aromatic amines such as pyridine, collidine, lutidine, pyrrole, indole and the like, and amines having a functional group such as N-ethylethanolamine, aminoethylisopropanolamine, diethylethanolamine, isopropanolamine, triisopropanolamine, diethanolamine, triethanolamine, morpholine, N-hydroxyethyl-morpholine, glycine, alanine, leucine, serine and the like. These amines can be used in an amount ranging from about 1/10,000 to about 10 mols per mol of the halopolyfluoroalkane (I) or (IV), but is preferably used in an amount ranging from 1/1,000 to 1 mol per mol of (I) or (IV), in order to perform the reaction smoothly and economically.

The reactions according to Processes 1 to 3 can be carried out in the absence of reaction solvents, but, if desired, an alcohol such as methanol, ethanol, propanol, t-butanol and the like, ethers such as tetrahydrofuran, diethyl ether and the like, or hydrocarbons such as hexane, cyclohexane, benzene and the like can be used.

The reaction according to Process 1, 2 or 3 can be carried out using about 0.5 to about 100 mols of the reactant (II), (IV) or (VII) per mol of the halopolyfluoroalkane (I) or (VI). The reaction proceeds smoothly at a temperature of from about 0° C. to about 200° C., but is preferably conducted at a temperature in the range of from room temperature (about 15° to 30° C.) to 120° C. from the standpoint of economy and reaction efficiency. The reaction time varies depending upon the reaction temperature used, but is generally completed in a relatively short period of time, for example, 2 or 3 minutes to about 72 hours.

In an alternative procedure, the reaction according to Process 3 can be carried out under radical generating conditions without using the metal-carbonyl complex catalyst. Such conditions can be achieved, for example, by radiating the reaction mixture with light or by conducting the reaction in the presence of a radical reaction initiator. When the reaction of Process 3 is carried out by radiating the reaction mixture with light, a light source having a wavelength of from about 210 to about 400 mm can be used, but, from the standpoint of efficiency of the reaction, it is preferred to use a light source having a wavelength of 300 to 380 mm, for example, a source from a high pressure mercury lamp. When the reaction of Process 3 is carried out in the presence of a radical reaction initiator, azobisisobutyronitrile (AIBN), di-t-butyl peroxide, benzoyl peroxide (BPO), etc. can be used as a radical reaction initiator. These initiators can be used in a catalytic amount, for example, about 1/1,000 to about 0.2 mol per mol of the halopolyfluoroalkane (VI).

The reaction under radical generating conditions can be carried out in the presence of the solvent as described above or in the absence of the solvent, and at a temperature of about −20° C. to about 60° C. while radiating the reaction mixture with light or at a temperature of about 60° C. to about 200° C. in the presence of a radical reaction initiator.

In the reaction according to Process 3, a silyl halide is formed as a by-product, but this compound can be easily converted into an allylsilane of the formula (VII) and, therefore, the Process 3 is very useful from the industrial standpoint.

The present invention is further illustrated in greater detail by the following Examples and Comparative Examples, but the present invention is not limited thereto. In these examples, the amount (mol %) of the catalyst and amine used is based on the amount of the halopolyfluoroalkane reactant used, "Py" represents pyridine, "EA" represents ethanolamine, "Me" represents methyl and "Et" represents ethyl.

COMPARATIVE EXAMPLE 1

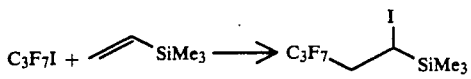

A mixture of 4.9 mg (0.05 mmol) of cuprous chloride, 296 mg (1.0 mmol) of 1-iodoheptafluoropropane, 100 mg (1.0 mmol) of vinyltrimethylsilane and 30.5 mg (0.5 mmol) of ethanolamine was heated in a sealed glass tube at 60° C. for 30 minutes. After opening the tube, the reaction mixture was quantitatively analyzed by gas chromatography and found to contain (1-iodo-3,3,4,4,5,5,5-heptafluoropentyl)trimethylsilane (Compound 1) in a yield of 2%.

COMPARATIVE EXAMPLE 2

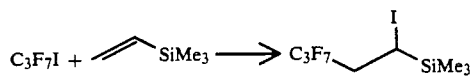

A mixture of 8.1 mg (0.05 mmol) of ferric chloride, 296 mg (1.0 mmol) of 1-iodoheptafluoropropane, 100 mg (1.0 mmol) of vinyltrimethylsilane and 30.5 mg (0.5 mmol) of ethanolamine was heated in a sealed glass tube at 60° C. for 30 minutes. After opening the tube, the reaction mixture was quantitatively analyzed by gas chromatography and found to contain (1-iodo-3,3,4,4,5,5,5-heptafluoropentyl)trimethylsilane (Compound 1) in a yield of only less than 1%.

EXAMPLE 1

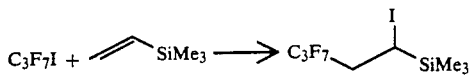

A mixture of 6.5 mg (0.013 mmol) of iron dodecacarbonyl [$Fe_3(CO)_{12}$], 296 mg (1.0 mmol) of 1-iodoheptafluoropropane (1.0 mmol), 100 mg (1.0 mmol) of vinyltrimethylsilane and 7.3 mg (0.12 mmol) of ethanolamine was heated in a sealed glass tube at 60° C. for 30 minutes. After opening the tube, the reaction mixture was quantitatively analyzed and found to contain (1-iodo-3,3,4,4,5,5,5-heptafluoropentyl)trimethylsilane (Compound 1) in a yield of 85%, together with a small amount of (1-iodomethyl-2,2,3,3,4,4,4-heptafluorobutyl)trimethylsilane.

EXAMPLES 2 TO 43

In the same manner as described in Example 1, a halopolyfluoroalkane and an olefin were reacted in the presence of a catalyst and an amine. The reactants, catalyst, amine as well as the reaction conditions used are shown in Table 1 below together with the yield of the product. In these examples, the addition product is generally obtained as a mixture of isomers, but only the main product is shown in Table 1 below. Also, the examples with an asterisk (*) was carried out on a 10-times scale of reaction.

TABLE 1

$$R^1-\underset{R^2}{\overset{F}{\underset{|}{C}}}-X + \diagup\!\!\!\diagdown R \longrightarrow R^1-\underset{R^2}{\overset{F}{\underset{|}{C}}}-\overset{I}{\underset{|}{C}}H_2\!\!-\!\!R$$

| Example No. | $R^1$ | $R^2$ | X | R | Catalyst (mol %) | Amine (mol %) | Reaction Temp. (°C.) | Reaction Time (hr.) | Addition Product (Yield %) |
|---|---|---|---|---|---|---|---|---|---|
| 2 | $C_2F_5$ | F | I | SiMe$_3$ | Fe$_3$(CO)$_{12}$ (1.3) | Py (4.0) | 60 | 0.5 | Compound 1 (75%) |
| 3 | $C_2F_5$ | F | I | SiMe$_3$ | Fe$_3$(CO)$_{12}$ (1.3) | Et$_3$N (12) | 60 | 0.5 | Compound 1 (74%) |
| 4 | $C_2F_5$ | F | I | SiMe$_3$ | Fe$_3$(CO)$_{12}$ (1.3) | Et$_2$NH (4.0) | 60 | 0.5 | Compound 1 (75%) |
| 5 | $C_2F_5$ | F | I | SiMe$_3$ | Fe$_3$(CO)$_{12}$ (1.3) | — | 60 | 3 | Compound 1 (71%) |
| 6 | $C_2F_5$ | F | I | SiMe$_3$ | Fe$_2$(CO)$_9$ (3.0) | — | 60 | 3 | Compound 1 (81%) |
| 7 | $C_2F_5$ | F | I | SiMe$_3$ | Fe(CO)$_5$ (7.0) | — | 100 | 3 | Compound 1 (95%) |
| 8 | $C_2F_5$ | F | I | SiMe$_3$ | Ru$_3$(CO)$_{12}$ (0.3) | — | 60 | 3 | Compound 1 (91%) |
| 9 | $C_2F_5$ | F | I | SiMe$_3$ | Co$_2$(CO)$_8$ (10.0) | EA (15) | 60 | 1 | Compound 1 (65%) |
| 10 | $C_7F_{15}$ | F | I | SiMe$_3$ | Fe$_3$(CO)$_{12}$ (1.3) | Py (4.0) | 60 | 0.5 | Compound 2 (76%) |
| 11 | $C_7F_{15}$ | F | I | SiMe$_3$ | Fe$_3$(CO)$_{12}$ (2.0) | — | 60 | 3 | Compound 2 (90%) |
| 12 | $C_7F_{15}$ | F | I | SiMe$_3$ | Fe(CO)$_5$ (4.0) | Py (4.0) | 100 | 0.5 | Compound 2 (82%) |
| 13 | $C_7F_{15}$ | F | I | SiMe$_3$ | Fe(CO)$_5$ (7.0) | — | 100 | 3 | Compound 2 (89%) |
| 14 | $C_7F_{15}$ | F | I | SiMe$_3$ | Ru$_3$(CO)$_{12}$ (0.3) | — | 60 | 3 | Compound 2 (64%) |
| 15* | F | F | I | SiMe$_3$ | Fe$_3$(CO)$_{12}$ (1.3) | Py (4.0) | 60 | 3 | Compound 3 (68%) |
| 16* | F | F | I | SiMe$_3$ | Fe$_3$(CO)$_{12}$ (2.0) | — | 60 | 18 | Compound 3 (71%) |
| 17* | F | F | I | SiMe$_3$ | Fe(CO)$_5$ (7.0) | — | 100 | 17 | Compound 3 (77%) |
| 18* | F | F | I | SiMe$_3$ | Ru$_3$(CO)$_{12}$ (0.3) | — | 60 | 18 | Compound 3 (89%) |
| 19 | BrCF$_2$ | F | I | SiMe$_3$ | Fe$_3$(CO)$_{12}$ (1.3) | EA (8.0) | 60 | 1 | Compound 4 (88%) |
| 20 | ClCF$_2$ | Cl | I | SiMe$_3$ | Fe$_3$(CO)$_{12}$ (1.3) | EA (12) | 60 | 0.5 | Compound 5 (93%) |
| 21 | BrCF$_2$ | Cl | Br | SiMe$_3$ | Fe$_3$(CO)$_{12}$ (1.3) | EA (12) | 60 | 5 | Compound 6 (77%) |
| 22* | F | Br | Br | SiMe$_3$ | Fe$_3$(CO)$_{12}$ (2.0) | EA (12) | 60 | 24 | Compound 7 (29%) |
| 23 | BrCF$_2$ | CF$_3$ | Br | SiMe$_3$ | Fe$_3$(CO)$_{12}$ (4.0) | EA (60) | 60 | 20 | Compound 8 (38%) |
| 24 | $C_2F_5$ | F | I | $C_4H_9$ | Fe$_3$(CO)$_{12}$ (1.3) | Py (4.0) | 60 | 1 | Compound 9 (76%) |
| 25 | $C_2F_5$ | F | I | $C_4H_9$ | Fe$_2$(CO)$_9$ (3.0) | — | 60 | 3 | Compound 9 (76%) |
| 26 | $C_2F_5$ | F | I | $C_4H_9$ | Fe(CO)$_5$ (7.0) | — | 100 | 3 | Compound 9 (91%) |
| 27 | $C_2F_5$ | F | I | $C_4H_9$ | Ru$_3$(CO)$_{12}$ (0.5) | — | 60 | 3 | Compound 9 (76%) |
| 28 | $C_7F_{15}$ | F | I | $C_4H_9$ | Fe$_3$(CO)$_{12}$ (2.3) | — | 60 | 3 | Compound 10 (76%) |
| 29 | $C_7F_{15}$ | F | I | $C_4H_9$ | Fe(CO)$_5$ (4.0) | Py (4.0) | 100 | 0.5 | Compound 10 (84%) |
| 30 | $C_7F_{15}$ | F | I | $C_4H_9$ | Ru$_3$(CO)$_{12}$ (0.3) | — | 60 | 3 | Compound 10 (52%) |
| 31* | F | F | I | $C_4H_9$ | Fe$_3$(CO)$_{12}$ (1.3) | Py (4.0) | 60 | 3 | Compound 11 (78%) |
| 32 | $C_2F_5$ | F | I | CH$_2$OH | Ru$_3$(CO)$_{12}$ (0.3) | — | 60 | 15 | Compound 12 (85%) |
| 33 | $C_2F_5$ | F | I | CH$_2$OH | Fe$_3$(CO)$_{12}$ (1.3) | — | 60 | 15 | Compound 12 (70%) |
| 34 | $C_2F_5$ | F | I | CH$_2$CH$_2$OH | Fe$_3$(CO)$_{12}$ (1.3) | Py (4.0) | 60 | 2 | Compound 13 (85%) |
| 35 | $C_2F_5$ | F | I | CH$_2$CH$_2$OH | Ru$_3$(CO)$_{12}$ (0.3) | — | 60 | 15 | Compound 13 (82%) |

TABLE 1-continued

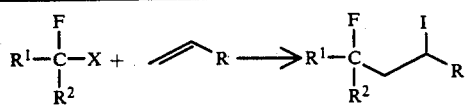

| Example No. | $R^1$ | $R^2$ | X | R | Catalyst (mol %) | Amine (mol %) | Reaction Temp. (°C.) | Reaction Time (hr.) | Addition Product (Yield %) |
| --- | --- | --- | --- | --- | --- | --- | --- | --- | --- |
| 36 | $C_2F_5$ | F | I | $CH_2OSiMe_3$ | $Fe_3(CO)_{12}$ (1.3) | — | 60 | 15 | Compound 14 (85%) |
| 37 | $C_2F_5$ | F | I | $CH_2OSiMe_3$ | $Ru_3(CO)_{12}$ (0.3) | — | 60 | 15 | Compound 14 (85%) |
| 38 | $C_2F_5$ | F | I | $CH_2OAc$ | $Ru_3(CO)_{12}$ (0.3) | — | 60 | 3 | Compound 15 (88%) |
| 39 | $C_2F_5$ | F | I | $CH_2OAc$ | $Fe_3(CO)_{12}$ (1.3) | — | 60 | 3 | Compound 15 (57%) |
| 40 | $C_2F_5$ | F | I | CH(Et)OH | $Ru_3(CO)_{12}$ (0.3) | — | 60 | 3 | Compound 16 (70%) |
| 41 | $C_2F_5$ | F | I | $CH_2COOMe$ | $Ru_3(CO)_{12}$ (0.3) | — | 60 | 18 | Compound 17 (51%) |
| 42 | $C_2F_5$ | F | I | $CH(OEt)_2$ | $Fe_3(CO)_{12}$ (2.0) | EA (12) | 60 | 3 | Compound 18 (78%) |
| 43 | $C_2F_5$ | F | I | OAc | $Fe_3(CO)_{12}$ (1.3) | Py (4.0) | 60 | 3 | Compound 19 (35%) |

EXAMPLE 44

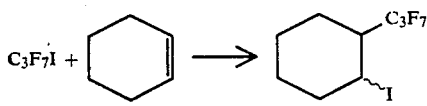

A mixture of 8.5 mg (0.0017 mmol) of iron dodecacarbonyl, 296 mg (1.0 mmol) of 1-iodoheptafluoropropane and 82 mg (1.0 mmol) of cyclohexene was heated in a sealed glass tube at 100° C. for 5 hours. After opening the glass tube, the reaction mixture was quantitatively analyzed by gas chromatography and found to contain 1-heptafluoropropyl-2-iodocyclohexane (Compound 20-a and Compound 20-b) in a yield of 36%.

EXAMPLE 45

A glass vessel containing 5.1 mg (0.008 mmol) of ruthenium carbonyl and 546 mg (1.0 mmol) of 1-iodoperfluorooctane was charged into an autoclave and the mixture was heated in an ethylene atmosphere under the pressure of 20 atms. at 60° C. for 20 hours. The reaction mixture was then quantitatively analyzed and found to contain 1,1,1,2,2,3,3,4,4,5,5,6,6,7,7,8,8-heptadecafluoro-10-iododecane (Compound 21) in a yield of 75%.

EXAMPLE 46

A glass vessel containing 17.9 mg (0.028 mmol) of ruthenium carbonyl and 546 mg (1.0 mmol) of 1-iodoperfluorooctane was charged into an autoclave and the mixture was heated in an ethylene atmosphere under the pressure of 20 atms. at 60° C. for 20 hours to obtain Compound 21 in a yield of 88%.

EXAMPLE 47

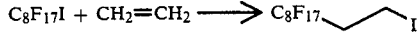

A glass vessel containing 33.7 mg (0.067 mmol) of iron dodecacarbonyl and 546 mg (1.0 mmol) of 1-iodoperfluorooctane was charged into an autoclave and the mixture was heated in an ethylene atmosphere under the pressure of 20 atms. at 60° C. for 20 hours to obtain Compound 21 in a yield of 87%.

EXAMPLE 48

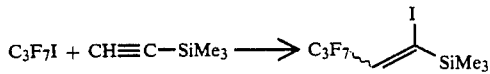

A mixture of 6.5 mg (0.013 mmol) of iron dodecacarbonyl, 296 mg (1.0 mmol) of 1-iodoheptafluoropropane, 98 mg (1.0 mmol) of trimethylsilylacetylene and 3.2 mg (0.04 mmol) of pyridine was heated in a glass tube at 60° C. for 30 minutes. After opening the glass tube, the reaction mixture was quantitatively analyzed by gas chromatography and found to contain 1-iodo-1-trimethylsilyl-3,3,4,4,5,5,5-heptafluoro-1-pentene (Compound 22) in a yield of 78%, together with a small amount of 1-iodo-2-trimethylsilyl-3,3,4,4,5,5,5-heptafluoro-1-pentene.

EXAMPLES 49 TO 76

In the same manner as described in Example 48, a halopolyfluoroalkane and an acetylene compound were reacted in the presence of a catalyst and an amine. The reactants, catalyst, amine as well as the reaction conditions used are shown in Table 2 below together with the yield of the product. In these examples, the addition product is generally obtained as a mixture of position and steric isomers, but only the position isomers which are mainly obtained in these examples are shown in Table 2.

TABLE 2

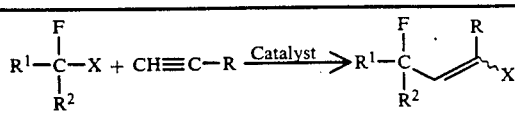

| Ex. No. | $R^1$ | $R^2$ | X | R | Catalyst (mol %) | Amine (mol %) | Reaction Temp. (°C.) | Reaction Time (hr.) | Addition Product (Yield %) |
|---|---|---|---|---|---|---|---|---|---|
| 49 | $C_2F_5$ | F | I | $SiMe_3$ | $Fe_3(CO)_{12}$ (1.3) | Py (4.0) | 60 | 1 | Compound 22 (82%) |
| 50 | $C_2F_5$ | F | I | $SiMe_3$ | $Fe_3(CO)_{12}$ (1.3) | EA (4.0) | 60 | 0.5 | Compound 22 (72%) |
| 51 | $C_2F_5$ | F | I | $SiMe_3$ | $Fe_3(CO)_{12}$ (1.3) | $Et_3N$ (12) | 60 | 0.5 | Compound 22 (53%) |
| 52 | $C_2F_5$ | F | I | $SiMe_3$ | $Fe_3(CO)_{12}$ (1.3) | $Et_2NH$ (4.0) | 60 | 0.5 | Compound 22 (64%) |
| 53 | $C_2F_5$ | F | I | $SiMe_3$ | $Fe_3(CO)_{12}$ (1.3) | $PhNH_2$ (12) | 60 | 0.5 | Compound 22 (20%) |
| 54 | $C_2F_5$ | F | I | $SiMe_3$ | $Fe_3(CO)_{12}$ (1.7) | — | 60 | 3 | Compound 22 (59%) |
| 55 | $C_2F_5$ | F | I | $SiMe_3$ | $Fe_2(CO)_9$ (2.0) | Py (4.0) | 60 | 0.5 | Compound 22 (72%) |
| 56 | $C_2F_5$ | F | I | $SiMe_3$ | $Fe(CO)_5$ (4.0) | Py (4.0) | 60 | 0.5 | Compound 22 (57%) |
| 57 | $C_2F_5$ | F | I | $SiMe_3$ | $Fe(CO)_5$ (7.0) | — | 100 | 3 | Compound 22 (93%) |
| 58 | $C_2F_5$ | F | I | $SiMe_3$ | $Ru_3(CO)_{12}$ (0.3) | Py (4.0) | 60 | 0.5 | Compound 22 (50%) |
| 59 | $C_7F_{15}$ | F | I | $SiMe_3$ | $Fe_3(CO)_{12}$ (3.3) | — | 60 | 3 | Compound 23 (62%) |
| 60 | $C_7F_{15}$ | F | I | $SiMe_3$ | $Fe(CO)_5$ (4.0) | Py (4.0) | 100 | 0.5 | Compound 23 (83%) |
| 61 | $C_7F_{15}$ | F | I | $SiMe_3$ | $Fe(CO)_5$ (7.0) | — | 100 | 3 | Compound 23 (92%) |
| 62* | F | F | I | $SiMe_3$ | $Fe_3(CO)_{12}$ (1.3) | Py (4.0) | 60 | 3 | Compound 24 (32%) |
| 63* | F | F | I | $SiMe_3$ | $Fe_3(CO)_{12}$ (2.3) | — | 60 | 18 | Compound 24 (40%) |
| 64 | $BrCF_2$ | F | I | $SiMe_3$ | $Fe_3(CO)_{12}$ (1.3) | EA (12) | 60 | 1 | Compound 25 (83%) |
| 65 | $BrCF_2$ | Cl | Br | $SiMe_3$ | $Fe_3(CO)_{12}$ (2.0) | EA (12) | 60 | 8 | Compound 26 (26%) |
| 66 | $C_2F_5$ | F | I | $C_5H_{11}$ | $Fe_3(CO)_{12}$ (1.3) | Py (4.0) | 60 | 1 | Compound 27 (75%) |
| 67 | $C_2F_5$ | F | I | $C_5H_{11}$ | $Fe(CO)_5$ (7.0) | — | 100 | 3 | Compound 27 (93%) |
| 68 | $C_7H_{15}$ | F | I | $C_5H_{11}$ | $Fe_3(CO)_{12}$ (2.8) | — | 60 | 3 | Compound 28 (87%) |
| 69 | $C_7H_{15}$ | F | I | $C_5H_{11}$ | $Fe(CO)_5$ (4.0) | Py (4.0) | 100 | 0.5 | Compound 28 (79%) |
| 70 | $C_7H_{15}$ | F | I | $C_5H_{11}$ | $Fe(CO)_5$ (7.0) | — | 100 | 3 | Compound 28 (91%) |
| 71* | F | F | I | $C_5H_{11}$ | $Fe_3(CO)_{12}$ (4.0) | Py (12) | 60 | 2 | Compound 29 (44%) |
| 72* | F | F | I | $C_5H_{11}$ | $Fe(CO)_5$ (7.0) | — | 100 | 17 | Compound 29 (39%) |
| 73 | $C_2F_5$ | F | I | Ph | $Fe(CO)_5$ (7.0) | — | 100 | 5 | Compound 30 (78%) |
| 74* | $C_2F_5$ | F | I | $CH_2CH_2OH$ | $Fe_3(CO)_{12}$ (1.3) | EA (12) | 60 | 2 | Compound 31 (66%) |
| 75 | $C_2F_5$ | F | I | $CH_2OH$ | $Fe_3(CO)_{12}$ (1.7) | — | 100 | 5 | Compound 32 (27%) |
| 76 | $C_2F_5$ | F | I | COOMe | $Fe_3(CO)_{12}$ (1.7) | — | 100 | 5 | Compound 33 (24%) |

EXAMPLE 77

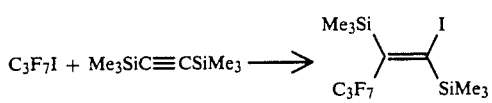

A mixture of 10.7 mg (0.2 mmol) of iron dodecacarbonyl, 2.96 g (10 mmol) of 1-iodoheptafluoropropane, 1.70 g (10 mmol) of ethanolamine was heated in a sealed glass tube at 60° C. for 14 hours. The reaction mixture was purified by silica gel column chromatography to obtain 2.66 g (57% yield) of 1,2-bis(trimethylsilyl)-1-iodo-3,3,4,4,5,5,5-heptafluoro-1-pentene (Compound 34) and 1.12 g (24% yield) of 1-trimethylsilyl-2-(iodomethyl)dimethylsilyl-3,3,4,4,5,5,5-heptafluoro-1-pentene (Compound 35).

The spectral data of the main products obtained in Examples 1 to 77 are shown in Tables 3 and 4 below. The compounds which were obtained as a mixture of two steric isomers are indicated by the symbols "a" and "b".

TABLE 3

| Compound No. | $^1H$ NMR ($CDCl_3$:TMS) (ppm) | $^{19}F$ NMR ($CDCl_3$:$CFCl_3$) (ppm) | Mass m/e (Relative Intensity) |
|---|---|---|---|
| 1 | 0.20 (s, 9H), 2.3–3.0 (m, 2H), 3.2 (m, 1H) | −81.0 (t, J=10Hz, 3F), −115.5 (m, 2F), −127.9 (m, 2F) | $M^+$ 396 (0), 73 (100) |
| 2 | 0.21 (s, 9H), 2.3–3.0 (m, 2H), 3.2 (m, 1H) | −81.0 (t, J=10Hz, 3F), −114.2 (m, 2F), −121.5 (m, 8F), −123.0 (m, 2F), −125.7 (m, 2F) | $M^+$ 646 (0), 73 (100) |
| 3 | 0.20 (s, 9H), 2.3–2.9 (m 2H), 3.1 (m, 1H) | −65.4 (t, J=9.5Hz) | $M^+$ 296 (3), 77 (100) |
| 4 | 0.20 (s, 9H), 2.3–3.0 (m, 2H), 3.21 (m, 1H) | −66.5 (m, 2F), −111.9 (d.d.d. t, J=256, 21, 12, 3.6Hz, 1H), −113.5 (d.d.d. t, J=256, 22, 12.4, 3.9Hz, 1F) | $M^+$ 408, 406 (0), 73 (100) |
| 5 | 0.21 (s, 9H), 2.3–3.0 (m, 2H), 3.3 (m, 1H) | −67.6 (m, 2F), −121.4 (m, 1F) | $M^+$ 382, 380, 378 (0), 73 (100) |
| 6 | 0.20 (s, 9H), 2.3–3.2 (m, 2H), 3.5 (m, 1H) | −61.5 (m, 2F), −118.4 (m, 1F) | $M^+$ 380, 378, 376, 374 (0), 73 (100) |
| 7 | 0.19 (s, 9H), 2.6–3.1 (m, 2H), 3.35 (m, 1H) | −42.0 (d.d.d. J=154, 13, 10Hz, 1F), −45.4 (dt, J=154, 15Hz, 1F) | $M^+$ 312, 310, 308, (0), 73 (100) |
| 8 | 0.20 (bs, 9H), 2.5–2.9 (m, 2H), 3.4 (m, 1H) | −59.2 (m, 2F), −74.9 (m, 3F), −177.2 (m, 1F) | $M^+$ 412, 410 (0), 73 (100) |
| 9 | 0.8–1.1 (m, 3H), 1.1–2.0 (m, 6H), 2.4–3.2 (m, 2H), 4.31 (quint., J=7Hz, 1H) | −81.0 (t, J=10Hz, 3F), −114.0 (m, 2F), −128.1 (m, 2F) | $M^+$ 380 (0), 43 (100) |

TABLE 3-continued

| Compound No. | $^1$H NMR (CDCl$_3$:TMS) (ppm) | $^{19}$F NMR (CDCl$_3$:CFCl$_3$) (ppm) | Mass m/e (Relative Intensity) |
|---|---|---|---|
| 10 | 0.8–1.1 (m, 3H), 1.1–2.0 (m, 6H), 2.4–3.2 (m, 2H), 4.32 (quint., J=7Hz, 1H) | −80.9 (t, J=10Hz, 3F), −112.5 (m, 2F), −121.0 (m, 8F), −122.9 (m, 2F), −125.7 (m, 2F) | M$^+$ 630 (0), 43 (100) |
| 11 | 0.8–1.1 (m, 3H), 1.1–2.0 (m, 6H), 2.83 (m, 2H), 4.20 (b. quint., J=7Hz, 1H) | −64.1 (t, J=9.8Hz) | M$^+$ 280 (0), 43 (100) |
| 12 | 2.05 (bs, 1H), 2.5–3.3 (m, 2H), 3.7 (bd, 2H), 4.41 (m, 1H) | −80.4 (t, J=10Hz, 2F), −113.6 (m, 2F), −127.2 (m, 2F) | M$^+$ 354 (3), 227 (100) |
| 13 | 1.73 (s, 1H), 2.03 (q, J=7Hz, 2H), 2.6–3.3 (m, 2H), 3.6–4.0 (m, 2H), 4.40 (quint., J=7Hz, 1H) | −80.5 (t, J=10Hz, 3F), −113.3 (m, 2F), −127.4 (m, 2F) | M$^+$ 368 (0), 31 (100) |
| 14 | 0.17 (s, 9H), 2.3–3.4 (m, 2H), 3.6–4.0 (m, 2H), 4.1–4.4 (m, 1H) | −80.5 (t, J=10Hz, 3F), −113.6 (m, 2F), −127.4 (m, 2F) | M$^+$ 426 (0), 73 (100) |
| 15 | 2.12 (s, 3H), 3.83 (m, 2H), 4.2–4.5 (m, 3H) | −80.4 (t, J=10Hz, 3F), −113.7 (m, 2F), −127.1 (m, 2F), | M$^+$ 396 (0), 43 (100) |
| 16 | 0.8–1.2 (m, 3H), 1.3–2.2 (m, 3H), 2.5–3.6 (m, 3H), 4.43 (m, 1H) | −80.4 (t, J=10Hz, 3F), −113.6 (m, 2F), −127.5 (m, 2F) | M$^+$ 382 (0), 57 (100) |
| 17 | 2.6–3.3 (m, 4H), 3.75 (s, 3H), 4.56 (quint., J=7Hz, 1H) | −80.3 (t, J=10Hz, 3F), −113.6 (m, 2F), −127.2 (m, 2F) | M$^+$ 396 (6), 59 (100) |
| 18 | 1.22 (t, J=7Hz, 6H), 1.7–3.0 (m, 3H), 3.57 (m, 4H), 4.52 (t, J=5Hz, 1H) | −80.9 (t, J=10Hz, 3F), −114.8 (m, 2F), −127.4 (m, 2F) | M$^+$ 426 (0), 103 (100) |
| 19 | 2.10 (s, 3H), 2.60 (td, J=18, 5.5Hz, 2H), 7.13 (t, J=5.5Hz, 1H) | −80.6 (t, J=10Hz, 3F), −113.3 (m, 2F), −127.6 (m, 2F) | M$^+$ 382 (0), 43 (100) |
| 20-a | 1.3–2.3 (m, 8H), 2.65 (m, 1H), 4.92 (m, 1H) | −80.8 (t, J=10Hz, 3F), −110.0 (m, 2F), −124.5 (m, 2F) | M$^+$ 378 (0), 251 (100) |
| 20-b | 1.2–2.4 (m, 9H), 4.70 (m, 1H) | −80.7 (t, J=10Hz, 3F), −117.9 (m, 2F), −125.3 (m, 2F) | M$^+$ 378 (1), 251 (100) |
| 21 | 2.3–3.1 (m, 2H), 3.1–3.4 (m, 2H) | −81.0 (t, J=Hz, 3F), −114.0 (m, 2F), −121.5 (m, 10F), −125.5 (m, 2F) | M$^+$ 574 (50), 69 (100) |

TABLE 4

| Compound No. | IR($\nu_{C=C}$) (cm$^{-1}$) | $^1$H NMR (CDCl$_3$:TMS) (ppm) | $^{19}$F NMR (CDCl$_3$:CFCl$_3$) (ppm) | Mass m/e (Relative Intensity) |
|---|---|---|---|---|
| 22-a | 1610 | 0.33 (t, J=1.4Hz, 9H), 7.28 (t, J=15Hz, 1H) | −80.5 (t, J=10Hz, 3F), −106.2 (m, 2F), −126.5 (m, 2F) | M$^+$ 394 (20), 73 (100) |
| 22-b |  | 0.27 (s, 9H), 6.74 (t, J=13Hz, 1H) | −80.5 (t, J=10Hz, 3F), −109.7 (m, 2F), −126.9 (m, 2F) |  |
| 23-a | 1590 | 0.33 (t, J=1.4Hz, 9H) 7.32 (bt, J=16Hz, 1H) | −80.9 (t, J=10Hz, 3F), −105.2 (m, 2F), −121.5 (m, 10F), −125.5 (m, 2F) | M$^+$ 644 (6), 77 (100) |
| 23-b |  | 0.26 (s, 9H), 6.78 (t, J=13Hz, 1H) | −80.9 (t, J=10Hz, 3F), −108.6 (m, 2F), −121.5 (m, 10F), −125.5 (m, 2F) |  |
| 24-a | 1600 | 0.33 (q, J=1Hz, 9H), 7.31 (q, J=8.4Hz, 1H) | −58.4 (bd, J=8,4Hz) | M$^+$ 294 (23), 189 (100) |
| 24-b |  | 0.24 (s, 9H), 6.80 (q, J=7.2Hz, 1H) | −61.6 (d, J=7.2Hz) |  |
| 25-a | 1590 | 0.33 (s, 1.5Hz, 9H), 7.33 (t, J=15Hz, 1H) | −66.1 (t, J=7Hz, 2F), −103.5 (m, 2F) | M$^+$ 406, 404 (3), 77 (100) |
| 25-b | 1605 | 0.27 (s, 9H), 6.78 (t, J=13Hz, 1H) | −66.3 (t, J=7Hz, 2F), −107.6 (d,t, J=13, 7Hz, 2F) | M$^+$ 406, 404 (12), 73 (100) |
| 26 | 1595 | 0.34 (t, J=3Hz, 9H), 6.99 (d, J=25Hz, 1H) | −60.8 (d,d, J=169, 11Hz, 1F), −63.0 (d,d, J=169, 13Hz, 1F), −177.7 (m, 1F) | M$^+$ 378, 376, 374, 372 (0), 77 (100) |
| 27-a | 1635 | 0.8–1.1 (m, 3H), 1.1–1.8 (m, 6H), 2.6 (m, 2H), 6.3 (bt, J=14Hz, 1H) | −80.9 (t, J=10Hz, 3F), −106.3 (m, 2F), −127.6 (m, 2F), | M$^+$ 392 (2), 55 (100) |
| 27-b | 1645 | 0.8–1.1 (m, 3H), 1.1–1.8 (m, 6H), 2.65 (m, 2H), 6.22 (bt, J=13Hz, 1H) | −80.7 (t, J=10Hz, 3F) −109.2 (m, 2F), −127.4 (m, 2F) | M$^+$ 392 (2), 55 (100) |
| 28-a | 1635 | 0.8–1.1 (m, 3H), | −80.8 (t, J=10Hz, 3F), | M$^+$ 642 (3), 55 (100) |

TABLE 4-continued

| Compound No. | IR($\nu_{C=C}$) (cm$^{-1}$) | $^1$H NMR (CDCl$_3$:TMS) (ppm) | $^{19}$F NMR (CDCl$_3$:CFCl$_3$) (ppm) | Mass m/e (Relative Intensity) |
|---|---|---|---|---|
| 28-b | 1640 | 1.1–1.8 (m, 6H), 2.63 (m, 2H), 6.32 (bt, J=14Hz, 1H) | −104.6 (m, 2F), −121.5 (m, 10F), −125.5 (m, 2F) | M$^+$ 642 (3), 55 (100) |
| 29-a | 1640 | 0.8–1.0 (m, 3H), 1.1–1.8 (m, 6H), 2.63 (m, 2H), 6.21 (bt, J=13Hz, 1H) | −80.9 (t, J=10Hz, 3F), −107.8 (m, 2F), −121.5 (m, 10F), −125.6 (m, 2F) | M$^+$ 292 (3), 41 (100) |
| 29-a | 1640 | 0.8–1.1 (m, 3H), 1.1–1.8 (m, 6H), 2.59 (bt, J=7Hz, 2H), 6.36 (q, J=7.7Hz, 1H) | −57.8 (bt, J=7.7Hz) | M$^+$ 292 (3), 41 (100) |
| 29-b | 1650 | 0.8–1.0 (m, 3H), 1.2–1.8 (m, 6H), 2.59 (m, 2H), 6.25 (q, J=7.0Hz, 1H) | −59.9 (bd, J=7.0Hz) | M$^+$ 292 (3), 55 (100) |
| 30-a | 1640 | 6.56 (t, J=13.5Hz, 1H), 7.1–7.4 (m, 5H) | −80.7 (t, J=10Hz, 3F), −105.8 (m, 2F), −127.3 (m, 2F) | M$^+$ 398 (2), 271 (100) |
| 30-b | 1625 | 6.48 (t, J=13Hz, 1H), 7.2–7.6 (m, 5H) | −80.4 (t, J=10Hz, 3F), −109.4 (m, 2F), −126.9 (m, 2F) | M$^+$ 398 (2), 271 (100) |
| 31-a | 1640 | 1.88 (bs, 1H), 2.93 (bt, J=6Hz, 2H), 3.38 (t, J=6Hz, 2H), 6.49 (t, J=14.2Hz, 1H) | −80.5 (t, J=10Hz, 3F), −105.6 (m, 2F), −127.0 (m, 2F) | M$^+$ 366 (10), 31 (100) |
| 31-b | 1645 | 1.68 (bs, 1H), 2.92 (m, 2H), 3.83 (t, J=6Hz, 2H), 6.37 (t, J=13Hz, 1H) | −80.3 (t, J=10Hz, 3F), −109.4 (m, 2F), −126.9 (m, 2F) | M$^+$ 366 (10), 31 (100) |
| 32-a | 1640 | 1.92 (bs, 1H), 4.33 (bs, 2H), 6.45 (t, J=14.3Hz, 1H) | −80.3 (t, J=10Hz, 3F), −105.2 (m, 2F), −127.0 (m, 2F) | M$^+$ 352 (58), 225 (100) |
| 32-b | 1660 | 2.0 (bs, 1H), 4.35 (m, 2H), 6.80 (t, J=13.5Hz, 1H) | −80.3 (t, J=10Hz, 3F), −108.2 (m, 2F), −126.8 (m, 2F) | M$^+$ 352 (79), 225 (100) |
| 33-a | 1640 | 3.88 (s, 3H), 6.46 (t, J=13.5Hz, 1H) | −80.4 (t, J=10Hz, 3F), −110.0 (m, 2F), −126.6 (m, 2F) | M$^+$ 380 (100) |
| 33-b | 1630 | 3.93 (s, 3H), 7.66 (t, J=13Hz, 1H) | −80.3 (t, J=10Hz, 3F), −111.1 (m, 2F), −126.7 (m, 2F) | M$^+$ 380 (100) |
| 34 | — | 0.36 (m, 9H), 0.46 (m, 9H) | −80.3 (t, J=10Hz, 3F), −95.9 (m, 2F), −121.4 (m, 2F) | M$^+$ 466 (0), 73 (100) |

EXAMPLE 78

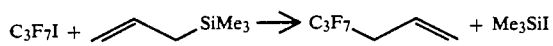

C$_3$F$_7$I + ⟶ C$_3$F$_7$ + Me$_3$SiI

A mixture of 6.5 mg (0.013 mmol) of iron dodecacarbonyl, 256 mg (1.0 mmol) of 1-iodoheptafluoropropane and 114 mg (1.0 mmol) of allyltrimethylsilane was heated in a sealed glass tube at 60° C. for 17 hours. After opening the tube, the reaction mixture was quantitatively analyzed by gas chromatography and found to contain 4,4,5,5,6,6,6-heptafluoro-1-hexene (Compound 35) in a yield of 75%.

EXAMPLES 79 to 90

In the same manner as described in Example 78, a halopolyfluoroalkane and allyltrimethylsilane were reacted in the presence of a catalyst and an amine. The reactant, catalyst, amine as well as the conditions used are shown in Table 5 below together with the yield of the product. The spectral data of the resulting compounds are shown in Table 6.

TABLE 5

$$R^1-\underset{R^2}{\underset{|}{\overset{F}{\overset{|}{C}}}}-X + \diagup\!\!\!\diagdown\!\!\!\diagup SiMe_3 \longrightarrow R^1-\underset{R^2}{\underset{|}{\overset{F}{\overset{|}{C}}}}-\diagup\!\!\!\diagdown\!\!\!\diagup + Me_3SiX$$

| Example No. | R$^1$ | R$^2$ | X | Catalyst | Amine (mol %) | Reaction Temp. (°C.) | Reaction Time (hr.) | Addition Product (Yield %) |
|---|---|---|---|---|---|---|---|---|
| 79 | C$_2$F$_5$ | F | I | Ru$_3$(CO)$_{12}$ (0.3) | — | 60 | 17 | Compound 35 (50%) |
| 80 | C$_2$F$_5$ | F | I | Fe$_3$(CO)$_{12}$ (2.0) | — | 60 | 12 | Compound 35 (80%) |
| 81 | C$_7$F$_{15}$ | F | I | Ru$_3$(CO)$_{12}$ (0.3) | — | 60 | 19 | Compound 36 (71%) |
| 82 | BrCF$_2$ | F | I | Ru$_3$(CO)$_{12}$ (0.3) | — | 60 | 3 | Compound 37 (67%) |
| 83 | BrCF$_2$ | F | I | Fe$_3$(CO)$_{12}$ (1.3) | — | 60 | 6 | Compound 37 (76%) |
| 84 | BrCF$_2$ | F | I | Fe$_3$(CO)$_{12}$ (1.3) | EA (12) | 60 | 3 | Compound 37 (82%) |
| 85 | BrCF$_2$ | Cl | Br | Ru$_3$(CO)$_{12}$ (0.3) | — | 60 | 6 | Compound 38 (59%) |
| 86 | BrCF$_2$ | Cl | Br | Fe$_3$(CO)$_{12}$ (1.3) | EA (12) | 60 | 6 | Compound 38 (50%) |
| 87 | ClCF$_2$ | Cl | I | Ru$_3$(CO)$_{12}$ (0.3) | — | 60 | 4 | Compound 39 (65%) |
| 88 | ClCF$_2$ | Cl | I | Fe$_3$(CO)$_{12}$ (1.3) | EA (12) | 60 | 4 | Compound 39 (80%) |

TABLE 5-continued $$R^1-\underset{R^2}{\overset{F}{\underset{|}{C}}}-X + \diagup\!\!\!\diagup\!\!\!\diagdown SiMe_3 \longrightarrow R^1-\underset{R^2}{\overset{F}{\underset{|}{C}}}\diagup\!\!\!\diagup\!\!\!\diagdown + Me_3SiX$$

| Example No. | $R^1$ | $R^2$ | X | Catalyst | Amine (mol %) | Reaction Temp. (°C.) | Reaction Time (hr.) | Addition Product (Yield %) |
|---|---|---|---|---|---|---|---|---|
| 89 | $BrCF_2$ | $CF_3$ | Br | $Fe_3(CO)_{12}$ (1.3) | EA (12) | 60 | 20 | Compound 40 (35%) |
| 90 | $ClCF_2$ | H | I | $Fe_3(CO)_{12}$ (1.3) | EA (12) | 60 | 3 | Compound 41 (66%) |

TABLE 6

| Compound No. | IR ($\nu_{C=C}$) (cm$^{-1}$) | $^1$H NMR (CDCl$_3$:TMS) (ppm) | $^{19}$F NMR (CDCl$_3$:CFCl$_3$) (ppm) |
|---|---|---|---|
| 35 | 1665 | 2.82 (t,d, J=18, 7Hz, 2H), 5.28 (bd, J=17Hz, 1H), 5.33 (bd, J=10Hz, 1H), 5.70 (m, 1H) | −81.0 (t, J=10Hz, 3F), −113.9 (m, 2F), −127.2 (m, 2F) |
| 36 | 1650 | 2.84 (t, d, J=18, 7Hz, 2H), 5.34 (bd, J=17Hz, 1H), 5.37 (bd, J=10Hz, 1H), 5.78 (d, d, t, J=17, 10, 7Hz, 1H) | −81.0 (t, J=10Hz, 3F), −112.5 (m, 2F), −123.3 (m, 10F), −125.6 (m, 2F) |
| 37 | 1650 | 2.85 (t, d, J=18, 7Hz, 2H) 5.31 (bd, J=17Hz, 1H), 5.34 (bd, J=10Hz, 1H), 5.77 (m, 1H) | −65.3 (bt, J=3.5Hz, 2F), −106.4 (t, t, J=18, 3.5Hz, 2F) |
| 38 | 1645 | 2.6–3.3 (m, 2H), 5.35 (bd, J=17Hz, 1H), 5.39 (bd, J=10Hz, 1H), 5.87 (m, 1H) | −60.6 (d, J=11.5Hz, 2F), −117.8 (d, q, J=25, 11.5Hz, 1F) |
| 39 | 1645 | 2.5–3.3 (m, 2H), 5.30 (bd, J=17Hz, 1H), 5.35 (bd, J=10Hz, 1H), 5.85 (m, 1H) | −70.0 (d, J=9.6Hz, 2F), −119.4 (d. d. t, J=21.4, 13.0, 9.6HZ, 1F) |
| 40 | 1645 | 2.93 (d.d, J=18, 7Hz, 2H), 5.3 (m, 2H), 5.7 (m, 1H) | −57.6 (m, 2F), −73.7 (m, 3F), −170.7 (m, 1F) |
| 41 | 1645 | 2.2–2.9 (m, 2H), 4.60 (d. m, J=46, 8Hz, 1H), 5.2 (m, 2H), 5.7 (m, 1H) | −65.3 (d.d.d, J=165, 15.4, 7.0Hz, 1F), −66.4 (d.d.d, J=165, 14.7, 6.1Hz, 1F), −190.5 (m, 1F) |

EXAMPLE 91

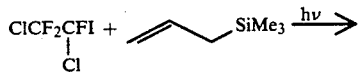

A mixture of 279 mg (1.0 mmol) of 1,2-dichloro-1-iodotrifluoroethane and 114 mg (1.0 mmol) of allyltrimethylsilane was sealed in a Pyrex glass tube and externally radiated with a high pressure mercury lamp (400 W) in an ice-bath for 3 hours to obtain 4,5-dichloro-4,5,5-trifluoro-1-pentene (Compound 39) in a yield of 60%.

EXAMPLE 92

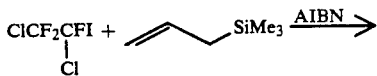

A mixture of 279 mg (1.0 mmol) of 1,2-dichloro-1-iodotrifluoroethane, 114 mg (1.0 mmol) of allyltrimethylsilane and 10 mg (0.06 mmol) of azobisisobutyronitrile (AIBN) was heated in a sealed glass tube at 80° C. for 3 hours. After cooling, 10 mg (0.06 mmol) of AIBN was added to the mixture, followed by heating in a sealed tube at 80° C. for 3 hours to obtain 4,5-dichloro-4,5,5-trifluoro-1-pentene (Compound 39) in a yield of 40%.

EXAMPLE 93

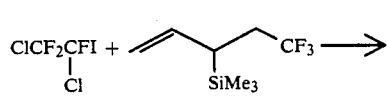

A mixture of 13.0 mg (0.026 mmol) of iron dodecacarbonyl, 9.2 mg (0.15 mmol) of ethanolamine, 279 mg (1.0 mmol) of 1,2-dichloro-1-iodotrifluoroethane and 196 mg (1.0 mmol) of 3-trimethylsilyl-5,5,5-trifluoro-1-pentene was heated in a sealed glass tube at 60° C. for 2 hours to obtain a cis-trans mixture of 1,1,1,6,7,7-hexafluoro-6,7-dichloro-3-heptene (Compound 42) in a yield of 88%.

$^1$H NMR (CDCl$_3$: TMS): δ2.6–3.4 (m, 4H), 5.5–6.1 (m, 2H). $^{19}$F NMR (CDCl$_3$: CFCl$_3$): δ-66.5, -66.9 (t, J=10.5 Hz, 3F), -67.0, -67.1 (bd, J=9.5 Hz, 2F), -120.0 (m, 1F).

EXAMPLE 94

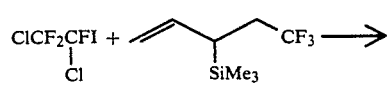

-continued

A mixture of 3.8 mg (0.006 mmol) of ruthenium carbonyl, 279 mg (1.0 mmol) of 1,2-dichloro-1-iodotrifluoroethane and 196 mg (1.0 mmol) of 3-trimethylsilyl-5,5,5-trifluoro-1-pentene was heated in a sealed glass tube at 60° C. for 2 hours to obtain a cis-trans mixture of 1,1,1,6,7,7-hexafluoro-6,7-dichloro-3-heptene (Compound 42) in a yield of 75%.

EXAMPLE 95

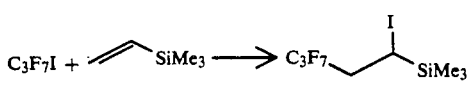

A mixture of 6.5 mg (0.013 mmol) of iron dodecacarbonyl, 296 mg (1.0 mmol) of 1-iodoheptafluoropropane, 100 mg (1.0 mmol) of vinyltrimethylsilane, 24.4 mg (0.4 mmol) of ethanolamine and 0.3 ml of ethanol was stirred in a sealed glass tube at 25° C. for 15 minutes. After opening the tube, the reaction mixture was quantitatively analyzed by gas chromatography and found to contain (1-iodo-3,3,4,4,5,5,5-heptafluoropentyl)trimethylsilane (Compound 1) in a yield of 91%.

EXAMPLES 96 to 102

In the same manner as described in Example 95, 1-iodoheptafluoropropane and vinyltrimethylsilane were reacted in the presence of a catalyst and amine in ethanol. The catalyst, amine as well as the reaction conditions used are shown in Table 7 below together with the yield of Compound 1.

EXAMPLE 104

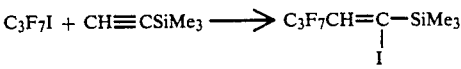

A mixture of 8.5 mg (0.025 mmol) of cobalt octacarbonyl, 296 mg (1.0 mmol) of 1-iodoheptafluoropropane, 98 mg (1.0 mmol) of trimethylsilylacetylene and 0.3 ml of ethanol was heated in a sealed glass tube at 60° C. for 3 hours. After opening the tube, the reaction mixture was quantitatively analyzed by gas chromatography and found to contain 1-iodo-1-trimethylsilyl-3,3,4,4,5,5,5-heptafluoro-1-pentene (Compound 22) in a yield of 77%.

EXAMPLE 105

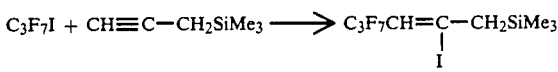

A mixture of 10 mg (0.02 mmol) of iron dodecacarbonyl, 296 mg (1.0 mmol) of 1-iodoheptafluoropropane, 112 mg (1.0 mmol) of propargyltrimethylsilane and 14.6 mg (0.24 mmol) of ethanolamine was heated in a sealed glass tube at 60° C. for 16 hours. After opening the tube, the reaction mixture was quantitatively analyzed by gas chromatography and found to contain 4,4,5,5,6,6,6-heptafluoro-2-iodo-2-hexenyltrimethylsilane (Compound 43) in a yield of 58%.

EXAMPLE 106

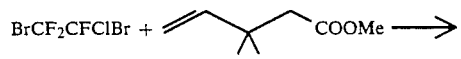

TABLE 7

| Example No. | Catalyst (mol %) | Amine (mol %) | Reaction Temp. (°C.) | Reaction Time (hr.) | Yield of Addition Product (%) |
|---|---|---|---|---|---|
| 96 | Fe$_3$(CO)$_{12}$ (1.3) | EA (12) | 25 | 2 | 85 |
| 97 | Fe$_3$(CO)$_{12}$ (1.3) | Et$_2$NH (40) | 25 | 1 | 96 |
| 98 | Fe$_3$(CO)$_{12}$ (1.3) | Et$_3$N (40) | 25 | 2 | 81 |
| 99 | Fe$_3$(CO)$_{12}$ (0.15) | L-Serine (5) | 60 | 0.25 | 77 |
| 100 | Co$_2$(CO)$_8$ (0.8) | EA (12) | 25 | 0.25 | 89 |
| 101 | Fe(CO)$_5$ (4) | EA (40) | 25 | 0.5 | 92 |
| 102 | Fe$_2$(CO)$_9$ (2) | EA (40) | 25 | 6 | 77 |

EXAMPLE 103

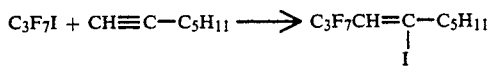

A mixture of 6.5 mg (0.013 mmol) of iron dodecacarbonyl, 296 mg (1.0 mmol) of 1-iodoheptafluoropropane, 96 mg (1.0 mmol) of 1-heptyne, 12.2 mg (0.2 mmol) of ethanolamine and 0.3 ml of ethanol was stirred in a sealed glass tube at 25° C. for 5 minutes. After opening the glass tube, the reaction mixture was quantitatively analyzed by gas chromatography and found to contain 1,1,1,2,2,3,3-heptafluoro-5-iodo-4-decene (Compound 27) in a yield of 62%.

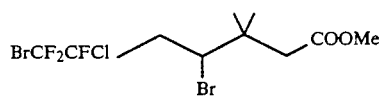

A mixture of 6.5 mg (0.013 mmol) of iron dodecacarbonyl, 276.5 mg (1.0 ml) of 1,2-dibromo-1-chlorotrifluoroethane, 142 mg (1.0 mmol) of methyl 3,3-dimethyl-4-pentenoate and 7.3 mg (0.12 mmol) of ethanolamine was heated in a sealed glass tube at 60° C. for 4 hours. After opening the tube, the reaction mixture was quantitatively analyzed by gas chromatography and found to contain methyl 3,3-dimethyl-4,7-dibromo-6-chloro-6,7,7-trifluoroheptanoate (Compound 44) in a yield of 78%.

EXAMPLE 107

$$ClCF_2CFClI + \underset{}{\diagup\!\!\!\diagdown}\!\!\diagup\!\!\!\!SiMe_2H \longrightarrow$$

$$ClCF_2CFCl\underset{}{\diagup\!\!\!\diagdown}\!\!\diagup\!\!\!\! + HMe_2SiI$$

A mixture of 3.8 mg (0.006 mmol) of ruthenium carbonyl, 279 mg (1.0 mmol) of 1,2-dichloro-1-iodotrifluoroethane, 128 mg (1.0 mmol) of (1,1-dimethyl-2-propenyl)dimethylsilane was heated in a sealed glass tube at 60° C. for 3 hours. After opening the tube, the reaction mixture was quantitatively analyzed by gas chromatography and found to contain 2-methyl-5,6-dichloro-5,6,6-trifluoro-2-hexene (Compound 45) in a yield of 82%.

While the invention has been described in detail and with reference to specific embodiments thereof, it will be apparent to one skilled in the art that various changes and modifications can be made therein without departing from the spirit and scope thereof.

What is claimed is:

1. A process for preparing a polyfluoroalkyl-substituted compound represented by the formula $$R^1-\underset{\underset{R^2}{|}}{\overset{\overset{F}{|}}{C}}-\underset{\underset{R^4}{|}}{\overset{\overset{R^3}{|}}{C}}-\underset{\underset{R^6}{|}}{\overset{\overset{R^5}{|}}{C}}-X$$

wherein X represents a chlorine atom, a bromine atom or an iodine atom; $R^1$ and $R^2$ each represents hydrogen, a halogen atom or a poly- or perfluoroalkyl group having 1 to 20 carbon atoms; and $R^3$, $R^4$, $R^5$ and $R^6$ each represents hydrogen, a halogen atom, a poly- or perfluorocarbon group having 1 to 20 carbon atoms, or a substituted or unsubstituted alkyl, vinyl, aryl, alkyloxy, acyloxy, amino, amide, silyl, silyloxy, alkylthio, alkoxycarbonyl, acyl, formyl or cyano group wherein the alkyl group has 1 to 10 carbon atoms and wherein the substituent is selected from the group consisting of an alkyl group having 1 to 5 carbon atoms, a halogen atom, an alkoxy group having 1 to 5 carbon atoms, a trialkylsilyl or trialkylsilyloxy group having 1 to 5 carbon atoms in each alkyl moiety, a hydroxy group, an alkoxycarbonyl group having 1 to 5 carbon atoms in the alkoxy moiety and an aryl group, which comprises reacting a halopolyfluoroalkane having 1 to 20 carbon atoms represented by the formula $$R^1-\underset{\underset{R^2}{|}}{\overset{\overset{F}{|}}{C}}-X$$

wherein X, $R^1$ and $R^2$ are as defined above, with an unsubstituted or substituted ethylene represented by the formula $$\underset{R^4}{\overset{R^3}{\diagdown}}C=C\underset{\diagdown R^6}{\overset{\diagup R^5}{}}$$

wherein $R^3$, $R^4$, $R^5$ and $R^6$ are as defined above, in the presence of a carbonyl complex of a metal of the Group VIII of the Periodic Table.

2. A process according to claim 1, wherein the reaction is conducted in the presence of an amine.

3. A process according to claim 1, wherein the carbonyl complex of the metal is selected from the group consisting of iron-carbonyl complexes, cobalt-carbonyl complexes and ruthenium-carbonyl complexes.

4. A process according to claim 1, wherein the reaction is conducted at a temperature of from room temperature to 120° C.

5. A process for preparing a polyfluoroalkyl-substituted compound represented by the formula $$R^1-\underset{\underset{R^2}{|}}{\overset{\overset{F}{|}}{C}}-\underset{}{\overset{\overset{R^7}{|}}{C}}=C\underset{\diagdown X}{\overset{\diagup R^8}{}}$$

wherein X represents a chlorine atom, a bromine atom or an iodine atom; $R^1$ and $R^2$ each represents hydrogen, a halogen atom or a poly- or perfluoroalkyl group having 1 to 20 carbon atoms; and $R^7$ and $R^8$ each represents hydrogen, a halogen atom, a poly- or perfluorocarbon group having 1 to 20 carbon atoms, or a substituted or unsubstituted alkyl, vinyl, aryl, alkyloxy, acyloxy, amino, amide, silyl, silyloxy, alkylthio, alkoxycarbonyl, acyl, formyl or cyano group wherein the alkyl group has 1 to 10 carbon atoms and wherein the substituent is selected from the group consisting of an alkyl group having 1 to 5 carbon atoms, a halogen atom, an alkoxy group having 1 to 5 carbon atoms, a trialkylsilyl or trialkylsilyloxy group having 1 to 5 carbon atoms in each alkyl moiety, a hydroxy group, an alkoxycarbonyl group having 1 to 5 carbon atoms in the alkoxy moiety and an aryl group, which comprises reacting a halopolyfluoroalkane having 1 to 20 carbon atoms represented by the formula $$R^1-\underset{\underset{R^2}{|}}{\overset{\overset{F}{|}}{C}}-X$$

wherein X, $R^1$ and $R^2$ are as defined above, with an unsubstituted or substituted acetylene compound represented by the formula $$R^7-C \equiv C-R^8$$

wherein $R^7$ and $R^8$ are as defined above, in the presence of a carbonyl complex of a metal of the Group VIII of the Periodic Table.

6. A process according to claim 5, wherein the reaction is conducted in the presence of an amine.

7. A process according to claim 5, wherein the carbonyl complex of the metal is selected from the group consisting of iron-carbonyl complexes, cobalt-carbonyl complexes and ruthenium-carbonyl complexes.

8. A process according to claim 1, wherein the reaction is conducted at a temperature of from room temperature to 120° C.

9. A process for preparing a polyfluoroalkyl-substituted compound represented by the formula

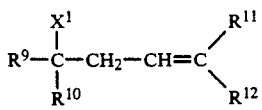

wherein $X^1$ represents a halogen atom, $R^9$ and $R^{10}$ each represents a poly- or perfluoroalkyl group having 1 to 20 carbon atoms, and $R^{11}$ and $R^{12}$ each represents hydrogen, an alkyl group having 1 to 5 carbon atoms or an aryl group, with the proviso that at least one of $R^9$, $R^{10}$ and $X^1$ represents a fluorine atom or a poly- or perfluoroalkyl group having 1 to 20 carbon atoms, which comprises reacting a halopolyfluoroalkane having 1 to 20 carbon atoms represented by the formula

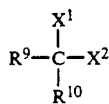

wherein $X^1$, $R^9$ and $R^{10}$ are as defined above, and $X^2$ represents a chlorine atom, a bromine atom or an iodine atom, with an allylsilane compound represented by the formula

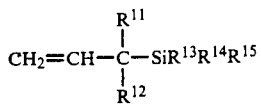

wherein $R^{11}$ and $R^{12}$ are as defined above, and $R^{13}$, $R^{14}$ and $R^{15}$ each represents hydrogen, an alkyl group having 1 to 10 carbon atoms or an aryl group.

10. A process according to claim 9, wherein the reaction is conducted in the presence of a carbonyl complex of a metal of the Group VIII of the Periodic Table.

11. A process according to claim 9, wherein the reaction is conducted in the presence of an amine.

12. A process according to claim 10, wherein said carbonyl complex of the metal is selected from the group consisting of iron-carbonyl complexes, cobalt-carbonyl complexes and ruthenium-carbonyl complexes.

13. A process according to claim 9, wherein said reaction is conducted under radical generating condition.

14. A process according to claim 13, wherein said radical generating condition is radiation with light.

15. A process according to claim 13, wherein said radical generating condition is effected in the presence of a radical reaction initiator.

* * * * *